(12) United States Patent
Claypool et al.

(10) Patent No.: US 7,520,880 B2
(45) Date of Patent: Apr. 21, 2009

(54) ADJUSTABLE SURGICAL SUPPORT BASE WITH INTEGRAL HINGE

(75) Inventors: Jody L. Claypool, Columbia City, IN (US); Chetan Rangaiah, Warsaw, IN (US); Matthew Foreman, Warsaw, IN (US)

(73) Assignee: Zimmer Technology, Inc., Warsaw, IN (US)

( * ) Notice: Subject to any disclaimer, the term of this patent is extended or adjusted under 35 U.S.C. 154(b) by 442 days.

(21) Appl. No.: 11/328,011

(22) Filed: Jan. 9, 2006

(65) Prior Publication Data
US 2007/0173849 A1    Jul. 26, 2007

(51) Int. Cl.
*A61B 17/58* (2006.01)
*A61B 17/70* (2006.01)
(52) U.S. Cl. ........................................ 606/88; 606/246
(58) Field of Classification Search ................ 606/87, 606/88, 86 R; 16/225, 231, 232, 246, 255
See application file for complete search history.

(56) References Cited

U.S. PATENT DOCUMENTS

| | | | |
|---|---|---|---|
| 4,211,228 A | 7/1980 | Cloutier | |
| 4,421,112 A | 12/1983 | Mains et al. | |
| 4,457,307 A | 7/1984 | Stillwell | |
| 4,467,801 A | 8/1984 | Whiteside | |
| 4,487,203 A | 12/1984 | Androphy | |
| 4,493,317 A | 1/1985 | Klaue | 606/69 |
| 4,501,266 A | 2/1985 | McDaniel | |
| 4,524,766 A | 6/1985 | Petersen | 606/88 |
| 4,566,448 A | 1/1986 | Rohr, Jr. | |
| 4,567,886 A | 2/1986 | Petersen | |
| 4,653,488 A | 3/1987 | Kenna | |
| 4,736,737 A | 4/1988 | Fargie et al. | |
| 4,759,350 A | 7/1988 | Dunn et al. | 606/82 |
| 4,841,975 A | 6/1989 | Woolson | 600/425 |
| 4,892,093 A | 1/1990 | Zarnowski et al. | |
| 4,907,577 A | 3/1990 | Wu | 606/87 |
| 4,913,137 A | 4/1990 | Azer et al. | |
| 4,952,213 A | 8/1990 | Bowman et al. | |
| 5,002,545 A | 3/1991 | Whiteside et al. | |
| 5,002,547 A | 3/1991 | Poggie et al. | 606/88 |

(Continued)

FOREIGN PATENT DOCUMENTS

EP    0538152    8/1995

(Continued)

OTHER PUBLICATIONS

U.S. Appl. No. 10/795,830, filed Mar. 8, 2004, Grimm.

(Continued)

*Primary Examiner*—Eduardo C Robert
*Assistant Examiner*—Ellen Rust
(74) *Attorney, Agent, or Firm*—Baker & Daniels LLP (57) ABSTRACT

An apparatus is provided for supporting a surgical component adjacent to a bone during a surgical procedure. The apparatus includes an integral body having a hinge platform, a hinge integral with the hinge platform; and a surgical component mounting portion integral with the hinge for rotation generally about a hinge axis relative to the hinge platform. An adjustment mechanism is operably connected between the hinge platform and the surgical component mounting portion to allow selective incremental rotation of the surgical component mounting portion relative to the hinge platform.

22 Claims, 4 Drawing Sheets

U.S. PATENT DOCUMENTS

| | | |
|---|---|---|
| 5,007,936 A | 4/1991 | Woolson .................... 128/898 |
| 5,037,423 A | 8/1991 | Kenna |
| 5,053,037 A | 10/1991 | Lackey |
| 5,092,037 A | 3/1992 | Pinkerton |
| 5,100,408 A | 3/1992 | Lackey |
| 5,116,338 A | 5/1992 | Poggie et al. ................. 606/90 |
| 5,154,717 A | 10/1992 | Matsen, III et al. ........... 606/53 |
| 5,171,277 A | 12/1992 | Roger ........................... 606/86 |
| 5,209,750 A * | 5/1993 | Stef ............................. 606/54 |
| 5,230,338 A | 7/1993 | Allen et al. ................. 600/429 |
| 5,234,433 A | 8/1993 | Bert et al. |
| 5,251,127 A | 10/1993 | Raab ........................ 606/130 |
| 5,275,603 A | 1/1994 | Ferrante et al. |
| 5,282,803 A | 2/1994 | Lackey |
| 5,305,203 A | 4/1994 | Raab ............................. 606/1 |
| 5,342,367 A | 8/1994 | Ferrante et al. |
| 5,342,368 A | 8/1994 | Petersen |
| 5,364,401 A | 11/1994 | Ferrante et al. |
| 5,364,402 A | 11/1994 | Mumme et al. |
| 5,411,505 A | 5/1995 | Mumme |
| 5,413,579 A | 5/1995 | Tom Du Toit ................. 606/87 |
| 5,417,694 A | 5/1995 | Marik et al. |
| 5,431,653 A | 7/1995 | Callaway |
| 5,431,656 A | 7/1995 | Clift, Jr. et al. |
| 5,445,642 A | 8/1995 | McNulty et al. |
| 5,454,816 A | 10/1995 | Ashby |
| 5,470,335 A | 11/1995 | Du Toit ........................ 606/73 |
| 5,474,559 A | 12/1995 | Bertin et al. .................. 606/89 |
| 5,484,446 A | 1/1996 | Burke et al. .................. 606/87 |
| 5,486,178 A | 1/1996 | Hodge |
| 5,486,180 A | 1/1996 | Dietz et al. ................... 606/87 |
| 5,514,139 A | 5/1996 | Goldstein et al. |
| 5,514,140 A | 5/1996 | Lackey |
| 5,551,429 A | 9/1996 | Fitzpatrick et al. .......... 600/426 |
| 5,562,674 A | 10/1996 | Stalcup et al. ................ 606/88 |
| 5,569,261 A | 10/1996 | Marik et al. |
| 5,584,838 A | 12/1996 | Rona et al. .................... 606/96 |
| 5,593,411 A | 1/1997 | Stalcup et al. ................ 606/88 |
| 5,597,379 A | 1/1997 | Haines et al. |
| 5,611,802 A | 3/1997 | Samuelson et al. |
| 5,628,750 A | 5/1997 | Whitlock et al. |
| 5,634,929 A | 6/1997 | Misko et al. ................. 606/130 |
| 5,643,272 A | 7/1997 | Haines et al. |
| 5,649,928 A | 7/1997 | Grundei |
| 5,669,914 A | 9/1997 | Eckhoff |
| 5,676,668 A | 10/1997 | McCue et al. |
| 5,681,316 A | 10/1997 | DeOrio et al. |
| 5,682,886 A | 11/1997 | Delp et al. .................. 600/407 |
| 5,683,397 A | 11/1997 | Vendrely et al. |
| 5,683,398 A | 11/1997 | Carls et al. |
| 5,720,752 A | 2/1998 | Elliott et al. |
| 5,743,915 A | 4/1998 | Bertin et al. .................. 606/88 |
| 5,743,916 A | 4/1998 | Greenberg et al. .......... 606/102 |
| 5,748,767 A | 5/1998 | Raab ........................... 382/128 |
| 5,788,700 A | 8/1998 | Morawa et al. |
| 5,810,831 A | 9/1998 | D'Antonio |
| 5,834,759 A | 11/1998 | Glossop .................... 250/203.1 |
| 5,871,018 A | 2/1999 | Delp et al. .................. 128/898 |
| 5,888,034 A | 3/1999 | Greenberg .............. 408/115 R |
| 5,891,158 A | 4/1999 | Manwaring et al. ......... 606/130 |
| 5,904,691 A | 5/1999 | Barnett et al. ............... 606/130 |
| 5,911,723 A | 6/1999 | Ashby et al. |
| 5,921,992 A | 7/1999 | Costales ...................... 606/130 |
| 5,995,738 A | 11/1999 | DiGioia, III et al. .......... 703/11 |
| 6,002,859 A | 12/1999 | DiGioia, III et al. .......... 703/11 |
| 6,022,377 A | 2/2000 | Nuelle et al. |
| 6,033,415 A | 3/2000 | Mittelstadt et al. .......... 606/130 |
| 6,056,756 A | 5/2000 | Eng et al. |
| 6,074,394 A | 6/2000 | Krause ......................... 606/86 |
| 6,077,270 A | 6/2000 | Katz |
| 6,081,741 A | 6/2000 | Hollis ......................... 600/424 |
| 6,090,114 A | 7/2000 | Matsuno et al. |
| 6,096,043 A | 8/2000 | Techiera et al. |
| 6,096,082 A | 8/2000 | Stegmuller et al. |
| 6,106,529 A | 8/2000 | Techiera |
| 6,162,228 A | 12/2000 | Durham ....................... 606/96 |
| 6,167,145 A | 12/2000 | Foley et al. .................. 382/128 |
| 6,234,429 B1 | 5/2001 | Yang |
| 6,267,762 B1 | 7/2001 | Millard et al. |
| 6,267,770 B1 | 7/2001 | Truwit ........................ 606/130 |
| 6,285,902 B1 | 9/2001 | Kienzle, III et al. .......... 600/427 |
| 6,338,716 B1 | 1/2002 | Hossack ..................... 600/459 |
| 6,342,056 B1 | 1/2002 | Mac-Thiong ................. 606/96 |
| 6,396,939 B1 | 5/2002 | Hu et al. ..................... 382/128 |
| 6,402,762 B2 | 6/2002 | Hunter ........................ 606/130 |
| 6,430,434 B1 | 8/2002 | Mittelstadt ................... 600/426 |
| 6,450,978 B1 | 9/2002 | Brosseau ..................... 600/595 |
| 6,458,135 B1 | 10/2002 | Harwin et al. |
| 6,477,400 B1 | 11/2002 | Barrick ....................... 600/426 |
| 6,490,467 B1 | 12/2002 | Bucholz ...................... 600/407 |
| 6,490,475 B1 | 12/2002 | Seeley ......................... 600/426 |
| 6,503,249 B1 | 1/2003 | Krause ......................... 606/62 |
| 6,514,259 B2 * | 2/2003 | Picard et al. .................. 606/88 |
| 6,533,790 B1 | 3/2003 | Liu ................................. 606/73 |
| 6,551,325 B2 | 4/2003 | Neubauer et al. |
| 6,554,837 B1 | 4/2003 | Hauri et al. |
| 6,575,980 B1 | 6/2003 | Robie et al. |
| 6,595,997 B2 | 7/2003 | Axelson, Jr. et al. |
| 6,638,281 B2 | 10/2003 | Gorek .......................... 606/96 |
| 6,648,896 B2 | 11/2003 | Overes et al. |
| 6,685,711 B2 | 2/2004 | Axelson, Jr. et al. |
| 6,695,848 B2 | 2/2004 | Haines |
| 6,712,824 B2 | 3/2004 | Millard et al. |
| 6,740,092 B2 | 5/2004 | Lombardo et al. |
| 6,758,850 B2 | 7/2004 | Smith et al. |
| 6,796,986 B2 | 9/2004 | Duffner |
| 6,859,661 B2 | 2/2005 | Tuke |
| 6,920,347 B2 | 7/2005 | Simon et al. |
| 6,932,823 B2 | 8/2005 | Grimm et al. |
| 6,942,700 B2 | 9/2005 | Williamson |
| 6,962,593 B2 | 11/2005 | Sanford et al. |
| 7,309,339 B2 * | 12/2007 | Cusick et al. ................. 606/88 |
| 2002/0133160 A1 | 9/2002 | Axelson, Jr. et al. |
| 2002/0133162 A1 | 9/2002 | Axelson, Jr. et al. |
| 2002/0151894 A1 | 10/2002 | Melkent ....................... 606/61 |
| 2002/0165552 A1 | 11/2002 | Duffner |
| 2003/0069585 A1 | 4/2003 | Axelson, Jr. et al. |
| 2003/0069591 A1 | 4/2003 | Carson et al. |
| 2003/0083667 A1 | 5/2003 | Ralph ........................... 606/96 |
| 2003/0171757 A1 | 9/2003 | Coon et al. |
| 2003/0181919 A1 | 9/2003 | Gorek .......................... 606/96 |
| 2003/0187351 A1 | 10/2003 | Franck |
| 2003/0212403 A1 | 11/2003 | Swanson |
| 2004/0039396 A1 | 2/2004 | Couture et al. |
| 2004/0073228 A1 | 4/2004 | Kienzle ....................... 606/96 |
| 2004/0122305 A1 | 6/2004 | Grimm ....................... 600/407 |
| 2004/0153066 A1 | 8/2004 | Coon et al. |
| 2004/0153083 A1 | 8/2004 | Nemec et al. |
| 2004/0172044 A1 | 9/2004 | Grimm ....................... 606/130 |
| 2005/0021039 A1 | 1/2005 | Cusick et al. |
| 2005/0049603 A1 | 3/2005 | Calton et al. |
| 2005/0055028 A1 | 3/2005 | Haines |
| 2005/0070910 A1 | 3/2005 | Keene |
| 2005/0149039 A1 | 7/2005 | Haines et al. |
| 2005/0149040 A1 | 7/2005 | Haines |
| 2005/0149041 A1 | 7/2005 | McGinley et al. |
| 2005/0171545 A1 | 8/2005 | Walsh et al. |
| 2005/0182415 A1 | 8/2005 | Steffensmeier et al. |
| 2005/0187557 A1 | 8/2005 | Collazo |
| 2005/0203528 A1 | 9/2005 | Couture et al. |
| 2005/0209598 A1 | 9/2005 | Grimm |
| 2005/0228393 A1 * | 10/2005 | Williams et al. .............. 606/87 |
| 2005/0234454 A1 | 10/2005 | Chin |
| 2005/0234465 A1 | 10/2005 | McCombs |

| | | | |
|---|---|---|---|
| 2005/0234466 | A1 | 10/2005 | Stallings |
| 2005/0273113 | A1 | 12/2005 | Kuczynski |
| 2005/0273114 | A1 | 12/2005 | Novak |

FOREIGN PATENT DOCUMENTS

| | | |
|---|---|---|
| EP | 0384562 | 7/1996 |
| EP | 0556998 | 6/1997 |
| EP | 0839501 | 7/1998 |
| EP | 0720834 | 6/1999 |
| EP | 1323386 | 7/2003 |
| EP | 1424042 | 2/2004 |
| EP | 1430842 | 6/2004 |
| EP | 1442712 | 8/2004 |
| EP | 0778751 | 5/2005 |
| EP | 1574177 | 9/2005 |
| EP | 1579812 | 9/2005 |
| JP | 11244315 | 9/1999 |
| WO | WO 96/07361 | 3/1996 |
| WO | WO 9629940 | 10/1996 |

OTHER PUBLICATIONS

U.S. Appl. No. 10/795,621, filed Mar. 8, 2004, Grimm.
U.S. Appl. No. 10/979,734, filed Nov. 2, 2004, Grimm.
U.S. Appl. No. 11/287,839, filed Nov. 28, 2005, Heavener.
Nexgen Complete Knee Solution, Intramedullary Instrumentation Surgical Technique, For The NexGen Cruciate Retaining & Legacy Posterior Stabilized Knee, Zimmer, Inc. 97-5973-102 Rev. 1 (1998).
Nexgen Complete Knee Solution, Posterior Reference, Multi-Referenced 4-in-1 Femoral Instrumentation; Posterior Reference Surgical Technique, For NexGen Cruciate Retaining & Legacy Posterior Stabilized Knees, Zimmer, Inc. 97-5973-402 Rev1 (1998).
Nexgen Complete Knee Solution, Micro-Mill Instrumentation Surgical Technique, For The NexGen Cruciate Retaining & Legacy Posterior Stabilized Knee, Zimmer, Inc. 97-5970-103 (1998).
Nexgen Complete Knee Solution, Revision Instrumentation Surgical Technique for Legacy Knee Constrained Condylar Knee, Zimmer, Inc. 97-5994-202 (2001).
Revision Knee Arthroplasty Surgical Guidelines, 2$^{nd}$ Edition, by Kelly Vince, M.D., John Insall, M.D., Robert Booth, Jr., M.D. and Giles Scuderi, M.D., Zimmer, Inc. 97-5224-03 Rev. 1 (1999).
Nexgen Complete Knee Solution, The Zimmer Institute Surgical Technique MIS Quad-Sparing Surgical Technique for Total Knee Arthroplasty, 2004.

* cited by examiner

ADJUSTABLE SURGICAL SUPPORT BASE WITH INTEGRAL HINGE

FIELD OF THE INVENTION

The present invention relates to instruments for use in surgical procedures. More particularly, the present invention relates to an adjustable support base for supporting a surgical component adjacent to a bone during a surgical procedure.

BACKGROUND

Degenerative and/or traumatic damage to skeletal joints or other locations within a patient's body may require surgical intervention. During such surgical intervention, it is often necessary to position and/or support a surgical component at a desired location relative to the surgical site. Surgical components may include implants, trial implants, drills, burrs, saws, lasers, thermal ablators, electrical ablators, retractors, clamps, cameras, microscopes, guides, and other surgical components. Surgical sites may include a hip joint, knee joint, vertebral joint, shoulder joint, elbow joint, ankle joint, digital joint of the hand or foot, jaw, fracture site, tumor site, and other suitable surgical sites. For example, damage to the articular cartilage of a skeletal joint can result in pain and restricted motion. Prosthetic joint replacement is frequently utilized to alleviate the pain and restore joint function. In this procedure, the damaged parts of the joint are cut away and replaced with prosthetic components. Typically a resection guide is used to guide a cutter such as a saw blade or burr to cut a desired portion of the bone to prepare a seating surface for a prosthetic component. The resection guide must be carefully positioned to guide the cut at the appropriate location. Prior art resection guides and related instruments are made of metal for durability and precision.

For example, during knee replacement surgery, an incision is made into the knee joint to expose the joint. Cutting guides are used to guide the removal of portions of the articular surfaces of the tibia and femur. Artificial joint components are positioned to replace the resected portions of the tibia and femur in order to establish the desired alignment and mechanics of the joint. In a total knee replacement, all of the articulating compartments of the joint are repaired with prosthetic components. However, often only one compartment of the knee joint, typically the medial compartment, is impaired. Thus, in a unicondylar knee replacement, only the damaged compartment is repaired with prosthetic bearing components.

Figure 1:
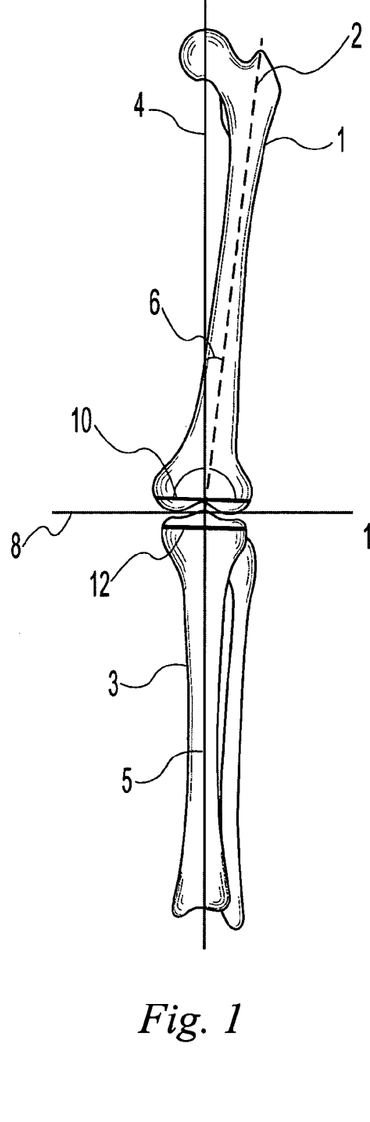
FIG. 1 is a front elevation view of a tibia and a femur showing axes of the knee joint.
Figure 2:
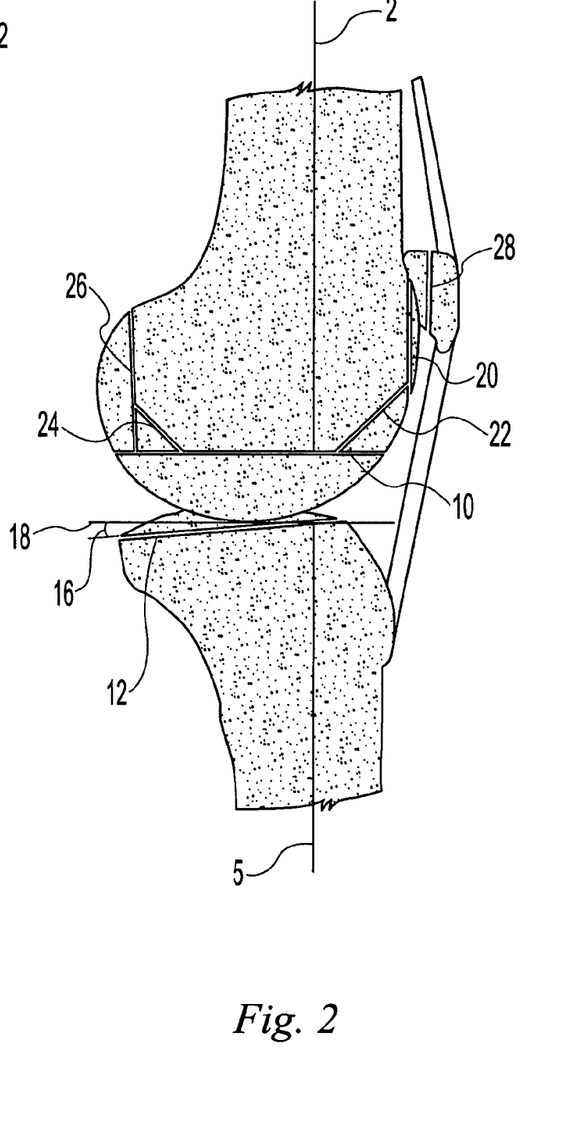
FIG. 2 is a side section view of a knee joint showing typical bone cuts used in replacing the joint surfaces.
Figure 3:
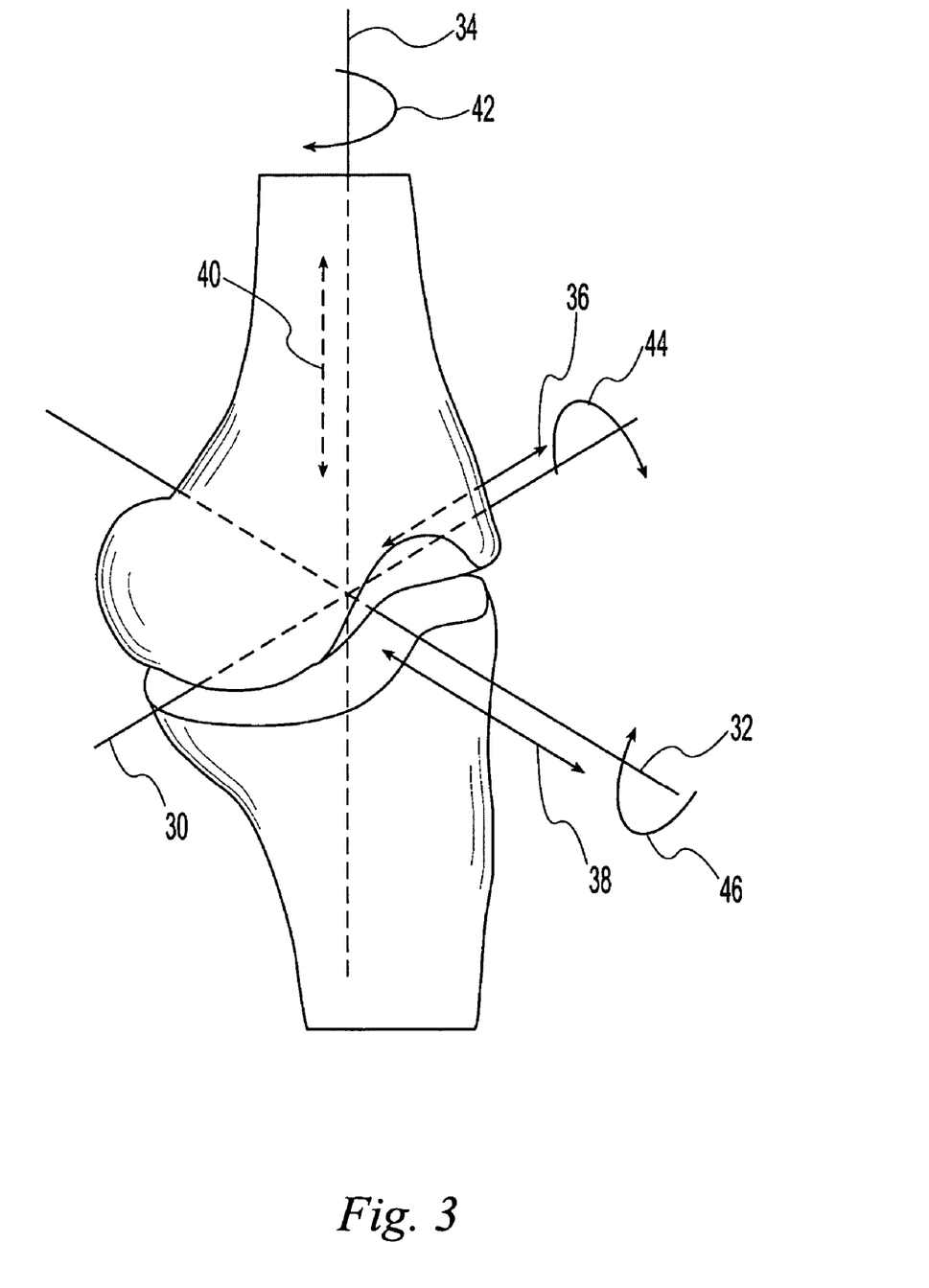
FIG. 3 is a perspective view of knee joint showing aspects of component positioning.

FIGS. 1-3 illustrate several aspects of the surgical anatomy of the knee joint. FIG. 1 illustrates various axes of the lower limb in the frontal plane. Axes can be defined for each segment of the lower limb. For example, the femur 1 has an anatomic axis 2 coinciding generally with its intramedullary canal. It also has a mechanical axis 4, or load axis, running from the center of the femoral head to the center of the knee. The angle 6 between these two axes 2, 4 in the frontal plane varies within the patient population but is on the order of 4-9°. The two axes 2, 4 are approximately superimposed in the sagittal plane (FIG. 2). Likewise, the tibia 3 has a mechanical axis 5 coinciding generally with its intramedullary canal. The mechanical axis 5 of the tibia runs from the center of the knee to the center of the ankle. The transverse axis, or joint line 8, about which the knee flexes, is parallel to a line through the medial and lateral femoral condyles and parallel to the tibial plateau. Typically, the distal femur and proximal tibia are resected to be parallel to the joint line 8, and thus perpendicular to the mechanical axes 4, 5 as indicated at 10 and 12. The intersection of the femoral and tibial mechanical axes 4, 5 may subtend a small angle relative to one another. However, the angle is small such that the axes 4, 5 are approximately collinear and may be treated as collinear for most purposes.

FIG. 2 illustrates the knee joint from the side or sagittal view and various bone cuts that may be made to align implant components. The distal femoral cut 10 is typically made perpendicular to the femoral axes 2, 4 in the sagittal plane. The proximal tibial resection 12 is typically cut to match the natural posterior slope, or rotation, 16 of the proximal tibia relative to the mechanical axes 4, 5. The amount of posterior slope 16 relative to a reference line 18 perpendicular to the mechanical axes 4, 5 varies in the patient population but is on the order of 7°. The distance between the distal femoral cut 10 and proximal tibial cut 12 along the mechanical axes 4,5 is the extension gap. Other cuts may be made depending on the components that are to be implanted. These include an anterior femoral cut 20, anterior femoral chamfer cut 22, posterior femoral chamfer cut 24, and posterior femoral cut 26. The patella 7 may also be cut 28 to allow for replacement of the patellar articular surface. In a unicondylar knee replacement, only the medial or lateral side of the knee joint is resurfaced. Furthermore, the trochlear, or patellar bearing, surface of the femur is typically left intact in a unicondylar procedure. Unicondylar implant designs vary, but typically only the distal femoral cut 10, posterior femoral chamfer cut 24, and posterior femoral cut 26 are needed to accommodate the unicondylar femoral implant.

FIG. 3 depicts six aspects of component positioning relative to a coordinate system in which the x-axis 30 corresponds approximately to the joint line 8, the z-axis 34 corresponds approximately to the mechanical axes 4 and 5, and the y-axis 32 is normal to the other two. Position along each of these axes is depicted by arrows. Position along the x, y, and z axes determines the medial/lateral (dx) 36, anterior/posterior (dy) 38, and proximal/distal (dz) 40 positioning of components respectively. Rotation about each of these axes is also depicted by arrows. Rotation about the z-axis (rz) 42 corresponds anatomically to external rotation of the femoral component, rotation about the x-axis (rx) 44 corresponds to extension plane rotation, and rotation about the y-axis (ry) 46 corresponds to varus/valgus rotation.

Many surgical procedures are now performed with surgical navigation systems in which sensors detect tracking elements attached in known relationship to an object in the surgical suite such as a surgical instrument, implant, or patient body part. The sensor information is fed to a computer that then triangulates the three dimensional position of the tracking elements within the surgical navigation system coordinate system. Thus, the computer can resolve the position and orientation of the object and provide position and orientation feedback for surgeon guidance. For example, the position and orientation can be shown superimposed on an image of the patient's anatomy obtained via X-ray, CT scan, ultrasound, or other imaging technology.

SUMMARY

The present invention provides an apparatus for supporting a surgical component adjacent to a bone during a surgical procedure. The apparatus includes an integral body having a hinge platform, a hinge integral with the hinge platform; and a surgical component mounting portion integral with the hinge for rotation generally about a hinge axis relative to the hinge platform. An adjustment mechanism is operably connected between the hinge platform and the surgical component mounting portion to allow selective incremental rotation of the surgical component mounting portion relative to the hinge platform.

BRIEF DESCRIPTION OF THE DRAWINGS

Various examples of the present invention will be discussed with reference to the appended drawings. These drawings depict only illustrative examples of the invention and are not to be considered limiting of its scope.

DESCRIPTION OF THE ILLUSTRATIVE EXAMPLES

Embodiments of an adjustable surgical support base include a body having a hinge platform, a hinge integral with the hinge platform, and a surgical component mounting portion integral with the hinge for rotation about the hinge relative to the hinge platform. An adjustment mechanism may be interposed between the hinge platform and the surgical component mounting portion to allow selective incremental rotation of the surgical component mounting portion relative to the hinge platform for positioning of the surgical component mounting portion and any attached surgical component. By providing the hinge platform, hinge, and mounting portion as a single piece, the precision of the hinge can be very high since there are no assembly tolerances as with hinge mechanisms made up of several parts. The unitary construction also dramatically reduces the parts count resulting in easier assembly and fewer parts that can be disassociated from the support base to become lost or contaminated during storage and during surgery. Fewer parts also results in less component wear. The unitary construction results in fewer crevices that can trap debris and that require special care during cleaning and sterilization. The unitary construction also results in lower manufacturing cost. The support base may be made as a disposable unit that is sold sterile and used for only one surgery to eliminate any need for post surgical disassembly, cleaning, and storage. The support base may be integrally formed all at once or it may be made of separate components that are combined into an integral body by adhesive bonding, heat bonding, welding, insert molding, press-fitting, and/or other suitable processes. The support base may be formed by machining, extruding, stamping, molding, and/or any other suitable forming method.

However, the integral construction is particularly suitable for molding of the integral components all at once to further reduce costs and improve uniformity. For example, the integral components may be cast, compression molded, injection molded, rotary molded, and/or otherwise formed in a mold or die from bulk materials. The support base may be made from metal, plastic, and/or other suitable materials sufficiently elastically deformable to permit formation of an integral living hinge. The support base may further be made of plastic to improve its compatibility with surgical imaging systems such as x-rays, fluoroscopy, and magnetic resonance imaging. For example, the support base maybe penetrable by x-rays and compatible with magnetic resonance imaging. For example, the support base may be made from polyolefins, polyesters, polyimides, polyamides, polyacrylates, poly(ketones), fluropolymers and/or other suitable polymers. For example, the support base may be injection molded from polyester, polypropylene, nylon, and/or other suitable polymers to yield a disposable yet precise hinge mechanism.

The hinge may define a bending portion over which the hinge bends. The hinge may include a cantilevered wall or web. The hinge may bend over a portion of the cantilevered wall generally about a hinge axis. The broader the portion of the wall over which the hinge bends, perpendicular to the hinge axis, the less circular will be the arc that the surgical component mounting portion transcribes since the instant axis of rotation shifts slightly with a bending hinge. The arc, while non-circular, is repeatable and precise. The non-circular arc may be advantageous in applications where non-circular motion is desired. Even though the instant axis of rotation shifts throughout the bending travel of the hinge, the shifting axis remains parallel to its original orientation and the hinge rotates generally about the original axis with the rotation remaining in the same plane throughout the hinge travel. Also, where the overall deflection of the hinge is small, for example less than ten degrees, the axis shift is also small. The hinge may define a discrete hinge line such that the hinge rotation occurs over a relatively small area of the cantilevered wall and therefore produces a more nearly circular motion. For example, the wall may include a narrowed portion to cause the hinge to bend at the narrowed portion. The narrowed portion may include a groove, channel, radius, and/or other suitable narrowed geometry. For example, the cantilevered wall may include radii in opposite sides of the wall to form a narrow web of material offering reduced stiffness at which the hinge bends.

The adjustment mechanism may include ratchets, wedges, pins moveable between multiple holes, screws, and/or other suitable adjustment mechanisms able to allow rotation of the surgical component mounting portion relative to the hinge platform. The adjustment mechanism may permit selective incremental rotation for precise positioning. For example, the adjustment mechanism may be operable to move the surgical component mounting portion between a plurality of positions relative to the hinge platform. The adjustment mechanism may be operable to move the surgical component mounting portion continuously and/or between discrete positions. In one example, the adjustment mechanism includes an adjustment screw threadably engaging the hinge platform. An end of the screw may bear against the surgical component mounting portion such that turning the screw so that it extends in a direction toward the surgical component mounting portion causes the surgical component mounting portion to rotate about the hinge. Turning the screw so that it retracts in a direction away from the surgical component mounting portion may allow the surgical component mounting portion to rotate the opposite direction about the hinge. The hinge may be sufficiently resilient that the surgical component mounting portion springs back toward an initial position. The adjustment mechanism may also engage the surgical component mounting portion for bi-directional axial force transmission such that it pushes the surgical component mounting portion when extended and pulls the surgical component mounting portion when retracted. The adjustment mechanism may include an end that is coupled to the surgical component mounting portion for free rotation and bidirectional axial force transmission. For example the adjustment mechanism may include an end that is retained by a clip, snap-fit, roll pin, cotter pin, clamp, and/or other suitable coupling arrangement. The hinge platform may include an adjustment mechanism support extending away from the bending portion of the hinge to support the adjustment mechanism at a position spaced from the hinge bending portion to increase the mechanical advantage of the adjustment mechanism relative to the hinge. The adjustment mechanism may be molded or machined similar to the integral components of the support base and may be made from metal, plastic, or other suitable materials. For example, both the integral components of the support base and the adjustment mechanism may be injection molded from plastic.

The support base may include additional hinges to allow further adjustability of the surgical component relative to the surgical site. For example, a second hinge similar to the first hinge can be included to provide a second axis of rotational adjustment. The hinge axes of the two hinges may be oriented in any relative orientation. They may be oriented transverse to one another to provide rotation in different planes. They may be oriented so that each hinge axis is related to adjustment in a different anatomic direction. For example, the hinges may be placed perpendicular to one another such that the support base can support rotation of the surgical component in two different anatomic planes such as the frontal plane and the sagittal plane. For example perpendicular hinges may be aligned with a medial/lateral axis and an anterior/posterior axis respectively to allow rotational adjustment about each of these axes. For example, in a knee surgical procedure, rotation about the medial/lateral axis permits extension plane rotational adjustment and rotation about the anterior/posterior axis permits varus/valgus rotational adjustment. Any number of hinges may be included in the support base and be oriented at any angle relative to one another to permit any desired rotational adjustment.

The support base may incorporate a translational adjustment mechanism. For example, the hinge platform may be coupled to a mounting block for translation relative to the mounting block by a translation adjustment mechanism. A translation adjustment mechanism may include a sliding joint, slip fit, telescoping tubes, screw jack, rack and pinion arrangement, linkage, ratchet, wedges, multiple pin receiving openings, and/or other suitable translation adjustment mechanism. For example, the hinge platform may include a slide that engages a slot formed on the mounting block and a screw jack for moving the slide within the slot so that operating the screw jack translates the hinge platform relative to the mounting block. Any number of translational adjustment mechanisms may be incorporated to permit translational adjustment in any desired direction. For example, in a knee surgical procedure, a translational adjustment mechanism may be oriented parallel to the proximal/distal axis of the knee to allow height adjustment of the hinge platform relative to the knee joint.

Figure 4:
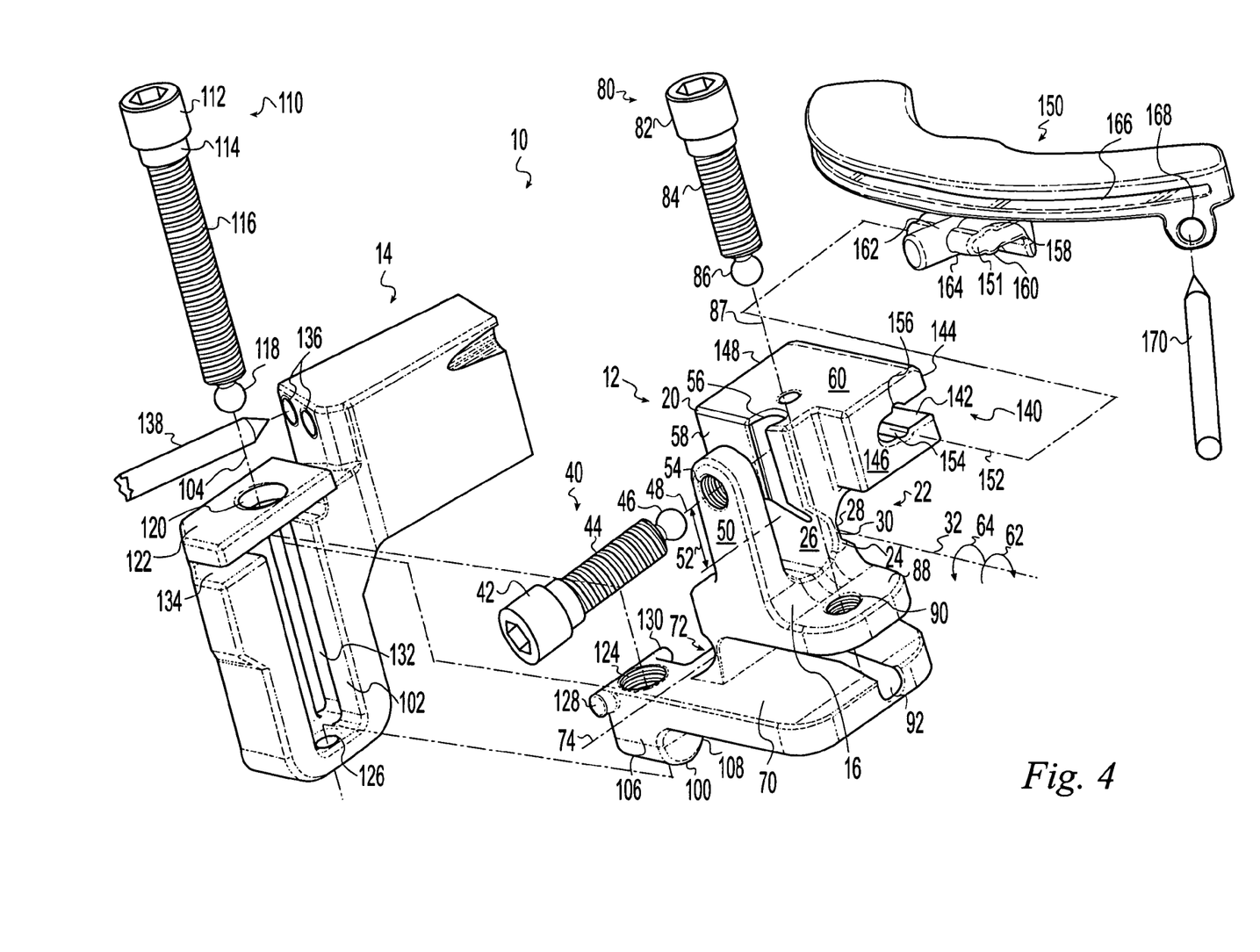
FIG. 4 is an exploded perspective view of an illustrative adjustable surgical support base according to the present invention.
Figure 5:
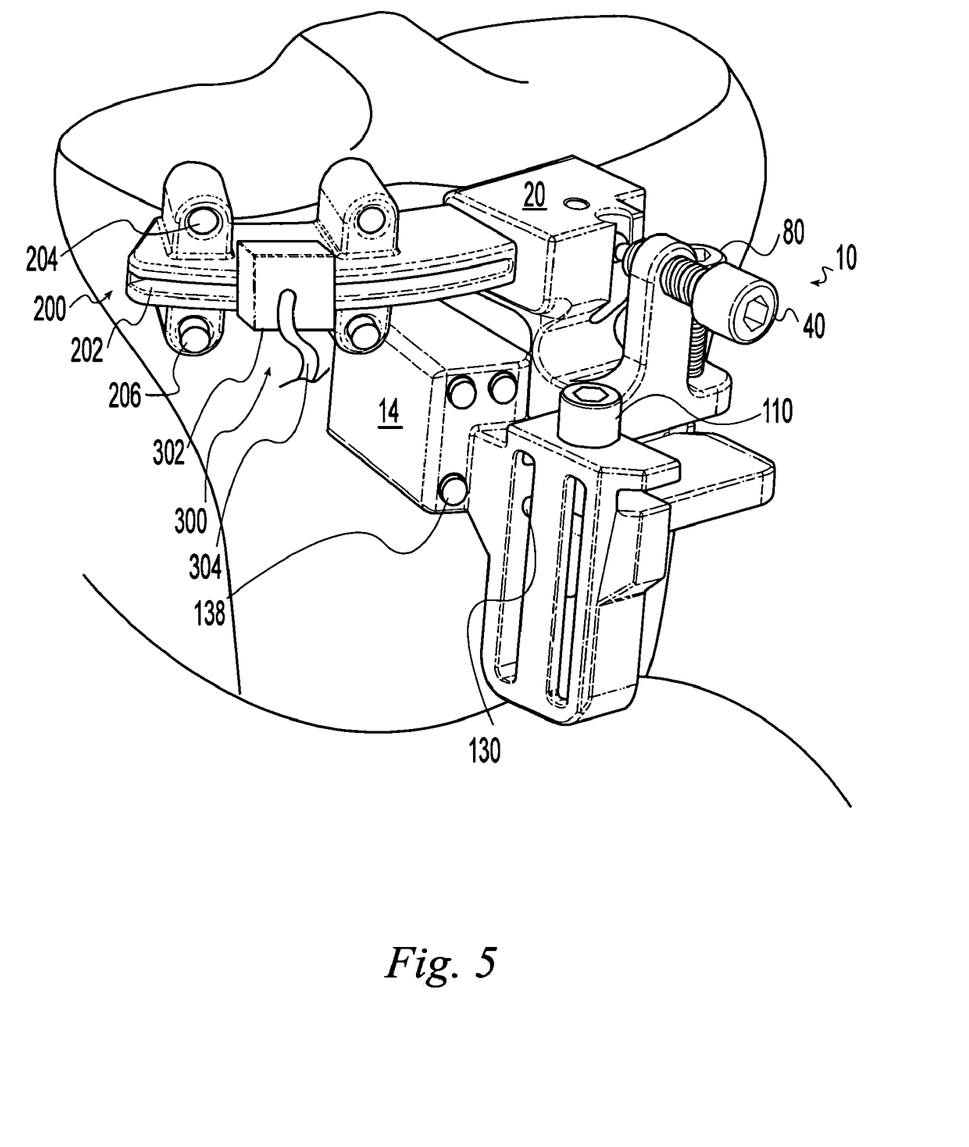
FIG. 5 is a perspective view of the assembled instrument of FIG. 4 mounted on a bone.

FIGS. 4 and 5 show an illustrative adjustable surgical support base 10 with an integral hinge. The support base 10 is shown with a femoral cut guide 150 in FIG. 4 and a tibial cut guide 200 in FIG. 5. The support base 10 is configured to support the femoral and tibial cut guides 150, 200 for positioning during knee replacement surgery. FIG. 5 illustrates the support base 10 in use supporting the tibial cut guide 200 for positioning during unicondylar knee surgery. However, the illustrative support base 10 is by way of example only and it is contemplated that the support base 10 may be used to support tibial and femoral cut guides during unicondylar knee replacement surgery and total knee replacement surgery. It is further contemplated that the support base 10 may be configured to support other surgical components at other surgical sites throughout the body.

The illustrative surgical support base 10 includes an adjustment sub-base 12 and a mounting sub-base 14. The adjustment sub-base 12 includes a first hinge platform 16 and a surgical component mounting block 20. The first hinge platform 16 includes a hinge 22 integral with the hinge platform 16. The hinge 22 includes a cantilevered wall 24 extending upwardly from the hinge platform 16 and connecting the surgical component mounting block 20 to the hinge platform 16. Radii are formed into opposite sides 26, 28 of the wall 24 to thin the wall 24 to a narrow web 30 to increase the flexibility of the wall 24 local to the web 30. The hinge 22 bends resiliently at the web 30 generally about a hinge axis 32. In the illustrative support base 10, the hinge axis 32 is configured to align parallel to the medial/lateral axis of the knee such that rotation about the hinge axis 32 corresponds to extension plane rotation.

An extension plane adjustment screw 40 includes a head 42, an elongated threaded shaft 44, and a ball tip 46 aligned generally along a screw axis 48. An extension plane adjustment screw support 50 projects upwardly from the first hinge platform 16 perpendicular to the hinge axis 32 to space the extension plane adjustment screw 40 away from the hinge axis 32 to increase the moment arm 52 that the extension plane adjustment screw 40 acts over and thus increase the mechanical advantage of the extension plane adjustment mechanism. The extension plane adjustment screw support 50 includes a threaded transverse through bore 54 directed toward the surgical component mounting block 20. The extension plane adjustment screw 40 threads into the bore 54 such that rotation of the extension plane adjustment screw 40 extends and retracts the screw tip 46 from the extension plane adjustment screw support 50 along the screw axis 48. The surgical component mounting block 20 includes a hemispherical groove 56 formed into the back 58 of the block 20 and extending from the top 60 of the block 20 downwardly perpendicular to the hinge axis 32. The sides of the hemispherical groove 56 transcribe more than 180 degrees such that the ball end 46 of the extension plane adjustment screw 40 is axially trapped in the hemispherical groove 56 to retain the block 20 and extension plane adjustment screw 40 together while permitting rotation and translation of the extension plane adjustment screw 50 relative to the block 20. Preferably, the ball end 46 is able to be axially snapped into the hemispherical groove 56 to ease assembly. Rotation of the extension plane adjustment screw 40 to extend the extension plane adjustment screw 40 in a direction toward the block 20 pushes the block 20 away from the extension plane adjustment screw support 50 and causes the block 20 to rotate clockwise 62 about the hinge axis 32. In the case of a tibial cut guide 200 supported on the anterior side of the tibia, this will tilt the extension plane downwardly and increase the posterior slope of the cut plane defined by the tibial cut guide 200. Rotation of the extension plane adjustment screw 40 to retract the adjustment screw 40 in a direction away from the block 20 pulls the block 20 toward the extension plane adjustment screw support 50 and causes the block 20 to rotate counter-clockwise 64 about the hinge axis 32. This will decrease the posterior slope of the tibial cut guide 200.

The illustrative support base 10 includes a second hinge platform 70 defining a second hinge 72 having a second hinge axis 74 perpendicular to the first hinge axis 32. In the illustrative support base 10, the second hinge axis 74 is aligned parallel to the anterior/posterior axis of the knee such that rotation about the second hinge axis 74 corresponds to varus/valgus rotation. The hinge 72 of the second hinge platform 70 is formed generally like the hinge 22 of the first hinge platform 16. A varus/valgus adjustment screw 80 includes a head 82, an elongated threaded shaft 84, and a ball tip 86 aligned generally along a screw axis 87. A varus/valgus adjustment screw support 88 extends outwardly from the first hinge platform 16 and includes a threaded bore 90. The varus/valgus adjustment screw 80 threads into the bore 90 and the ball tip 86 of the varus/valgus adjustment screw engages a hemispherical groove 92 formed in the second hinge platform 70 and extending perpendicular to the second hinge axis 74. Rotation of the varus/valgus adjustment screw 80 causes the first hinge platform 16 to rotate about the second hinge axis 74 relative to the second hinge platform in relative varus/valgus rotation.

The adjustment sub-base 12 includes a slide 100 that engages a slot 102 in the mounting sub-base 14 for translation along a translation axis 104. The slide 100 has opposing side walls 106, 108 that fit closely within the slot 102 for relatively slop free translation. In the illustrative support base 10, the translation axis 104 is aligned generally with the proximal/distal axis of the knee such that translation of the adjustment sub-base 12 parallel to the translation axis varies the height of the adjustment sub-base 12 relative to the proximal/distal axis. A height adjustment screw 110 includes a head 112, a bearing portion 114, a threaded elongated shaft 116, and a ball end 118 all generally aligned along the translation axis 104. The height adjustment screw 110 is mounted for rotation in the mounting sub-base 14 with the bearing portion 114 journaled in a through bore 120 in the top 122 of the mounting sub-base 14. The height adjustment screw 110 extends along the slot 102 and threads through a bore 124 in the slide 100. The ball end 118 of the height adjustment screw 110 snaps into a bore 126 in the bottom of the mounting sub-base 14 to retain the height adjustment screw 110 axially in the slot 102. The height adjustment screw 110 retains the slide 100 in the slot 102. The illustrative slide 100 includes cylindrical ears 128, 130 projecting outwardly from the sides 106, 108 of the slide to engage opposing grooves 132 (one shown) parallel to the slot 102 to further supplementally retain the slide in the slot 102. A transverse assembly notch 134 provides clearance for inserting the ears 128, 130 into the grooves 132. Rotation of the height adjustment screw 110 causes the slide, and thus the adjustment sub-base 12, to translate up and down along the translation axis relative to the mounting sub-base 14. The mounting sub-base 14 includes fixation holes 136 for receiving fixation pins 138 to secure the support base 10 to a bone.

The surgical component mounting block 20 defines a surgical component attachment mechanism 140 including a slot 142 formed into the front 144 of the block 20 and extending from one side 146 of the block 20 to the other side 148 to receive a tab 151 extending from the cut guides 150, 200 (tab 151 not shown on tibial cut guide 200) in slip-fit engagement along a slip-fit axis 152. The slot 142 includes top and bottom longitudinal grooves 154, 156 extending from side 146 to side 148 to receive longitudinal ribs 158, 160 projecting from the top and bottom of the tab 151 to resist the tab 151 pulling out of the front of the slot 142 transverse to the slip-fit axis 152. Top and bottom transverse grooves (not shown) at the center of the slot 142 receive top and bottom transverse ribs 162, 164 so that the tab 151 forms a sliding snap fit with the slot 142 to resist side-to-side slipping when the transverse ribs 1621, 164 snap into the center of the slot 142. The femoral and tibial cut guides 150, 200 include saw blade slots 166, 202 defining cut planes. The saw blade slots 166, 202 are able to guide a saw blade (not shown) within the cut planes to cut the femur and tibia respectively. Fixation holes 168, 204 are formed through the cut guides 150, 200 to receive fixation pins 170, 206, screws, and/or other suitable fasteners to secure the cut guides 150, 200 to a bone. The tibial cut guide 200 has fixation holes 204 above and below the saw blade slot 202 to facilitate flipping the guide for left and right mounting. The femoral cut guide 150 has a fixation hole at each end (one shown) of the guide to secure its position relative to the femur. The femoral and tibial cut guides 150, 200 may be made of the same choice of materials as the support base 10. For example, they may be made of metal for durability or made of plastic for disposability and to facilitate their use with intraoperative imaging.

A surgical navigation system may be used along with the support base 10 to guide positioning of a surgical component. For example, a tracking element may be permanently or removably mounted anywhere on the cut guides 150, 200 or the surgical component mounting block 20. However, to reduce positioning errors and simplify use, it is preferable to mount the tracking element as close as possible to the saw blade slots 166, 202. For example, the tracking element may be embedded within or attached to the femoral or tibial cut guides 150, 200. In the illustrative apparatus, a tracking assembly 300 (FIG. 5) includes a housing 302 containing one or more tracking elements such as electromagnetic coils. A cable 304 connects the tracking assembly 300 to the surgical navigation system. A plate (not shown) extends from the housing 302 to engage the saw slots 166, 202 in slip fit relationship to position the tracking assembly relative to slots 166, 202.

In use (FIG. 5), a surgical component, such as the tibial cut guide 200, is attached to the surgical component mounting block 20. The support base 10 is positioned adjacent a surgical site, for example the knee joint, and secured to the bone with pins 138. This initial positioning may be done manually or with the aid of an alignment instrument such as an alignment rod, feeler gauge, fluoroscopy, surgical navigation, and/or other suitable alignment instrument. For example, the tracking assembly 300 may be attached to the tibial cut guide 200 and the surgical navigation system activated to indicate when the initial positioning is within the adjustment limits of the support base 10. With the support base 10 secured, the extension plane adjustment screw 40 is rotated to set the posterior slope of the cut plane, the varus/valgus adjustment screw 80 is rotated to set the varus/valgus angle of the cut plane, and the height adjustment screw 110 is rotated to set the depth of the cut plane. The final positioning of the tibial cut guide 200 may be done manually or with the aid of an alignment instrument. For example, the surgical navigation system may be activated to indicate when the cut plane is in a desired position relative to the knee joint. The support base 10 provides a solid foundation and precise adjustment to aid in accurately navigating the tibial cut guide 200 into its final position. Additional fixation pins 206 may be inserted through the tibial cut guide to further secure it to the bone. The tracking assembly 300 is removed from the saw blade slot 202 and a saw blade is guided in the saw blade slot 202 to cut the tibia.

Although examples of an adjustable surgical support base and its use have been described and illustrated in detail, it is to be understood that the same is intended by way of illustration and example only and is not to be taken by way of limitation. The invention has been illustrated to aid in navigating cut guides to a desired position adjacent to the knee joint during knee replacement surgery. However, the adjustable surgical support base may be configured to support other surgical components adjacent other surgical sites and for use with or without surgical navigation. Accordingly, variations in and modifications to the adjustable surgical support and its use will be apparent to those of ordinary skill in the art, and the following claims are intended to cover all such modifications and equivalents.

What is claimed is:

1. An apparatus for supporting a surgical component adjacent to a bone during a surgical procedure, the apparatus comprising:
   an integral body comprising:
      a hinge platform;
      a first living hinge integral with the hinge platform;
      a surgical component mounting portion integral with the first hinge for rotation generally about a first axis relative to the hinge platform; and
      a first adjustment mechanism operably connected between the hinge platform and the surgical component mounting portion to allow selective incremental rotation of the surgical component mounting portion relative to the hinge platform.

2. The apparatus of claim 1 wherein the integral body is formed as a single unitary component.

3. The apparatus of claim 2 wherein the integral body comprises an integrally molded plastic body.

4. The apparatus of claim 1 wherein the integral body is penetrable by x-rays and compatible with magnetic resonance imaging.

5. The apparatus of claim 1 wherein the first hinge comprises a cantilevered wall having a first end and a second end, the wall arising from the hinge platform at the first end and the wall supporting the surgical component mounting portion at the second end.

6. The apparatus of claim 5 wherein the wall further comprises a narrowed portion between the first and second ends, the first hinge bending at the narrowed portion.

7. The apparatus of claim 6 wherein the narrowed portion is defined by opposing radii formed on opposite sides of the wall.

8. The apparatus of claim 1 wherein the first adjustment mechanism comprises an adjustment screw threadably mounted to the hinge platform, the adjustment screw having an end contacting the surgical component mounting portion such that rotating the adjustment screw causes the surgical component mounting portion to rotate about the first hinge.

9. The apparatus of claim 8 wherein the first hinge is resiliently biased against the adjustment screw.

10. The apparatus of claim 8 further comprising an adjustment screw support projecting from the hinge platform, the adjustment screw support defining an adjustment bore having an adjustment axis spaced away from the hinge axis a moment arm distance, the adjustment screw threadably engaging the adjustment bore for translation along the adjustment axis.

11. The apparatus of claim 8 wherein the adjustment screw engages the surgical component mounting portion in bi-directional axial force transmitting relationship.

12. The apparatus of claim 11 wherein the end of the adjustment screw includes a hemispherical ball tip and the surgical component mounting portion defines a hemispherical groove, the ball tip engaging the hemispherical groove for bi-directional axial force transmission.

13. The apparatus of claim 8 wherein the integral body and screw both comprise molded plastic.

14. The apparatus of claim 1 further comprising a second hinge integral with the body, the second hinge supporting rotation generally about a second axis.

15. The apparatus of claim 14 wherein the first axis and second axis are perpendicular to one another.

16. The apparatus of claim 15 further comprising a mounting base and a translational adjustment mechanism operably connected between the mounting base and the integral body, the translational adjustment mechanism being operable to translate the integral body relative to the mounting base.

17. The apparatus of claim 16 wherein the mounting base includes a fixation mechanism operable to secure the mounting base to the bone.

18. The apparatus of claim 16 wherein the translational adjustment mechanism comprises a slide slip-fit within a slot and a screw jack operable to translate the slide within the slot.

19. The apparatus of claim 1 further comprising a cut guide mounted to the surgical component mounting portion.

20. An apparatus for supporting a cut guide adjacent to the knee joint during knee joint replacement surgery, the knee joint comprising a tibia and a femur and having a medial/lateral axis, an anterior/posterior axis, and a proximal/distal axis, rotation about the medial/lateral axis corresponding to extension plane rotation, and rotation about the anterior/posterior axis corresponding to varus/valgus rotation, the apparatus comprising:
   a mounting base mountable to a bone;
   an integral body mounted to the mounting base, the integral body comprising:
      a first living hinge generally defining a first hinge axis;
      a surgical component mounting portion integral with the first hinge for rotation generally about the first hinge axis relative to the mounting base;
      a second hinge integral with the first hinge, the second hinge generally defining a second hinge axis oriented generally transverse to the first hinge axis, the surgical component mounting portion being rotatable generally about the second hinge axis relative to the mounting base;
   a first rotational adjustment mechanism operably connected to the integral body, the first rotational adjustment mechanism being operable to effect selective incremental rotation of the surgical component mounting portion about the first hinge axis relative to the mounting base;
   a second rotational adjustment mechanism operably connected to the integral body, the second rotational adjustment mechanism being operable to effect selective incremental rotation of the surgical component mounting portion about the second hinge axis relative to the mounting base; and a cut guide mounted to the surgical component mounting portion, the cut guide defining a cut plane.

21. The apparatus of claim 20 further comprising a translational adjustment mechanism operably connected between the integral body and the mounting base, the translational adjustment mechanism being operable to effect selective incremental translation of the integral body relative to the mounting base along a translation axis, the translation axis being oriented generally transverse to both the first and second hinge axes.

22. The apparatus of claim 21 wherein the mounting base is mountable on a bone relative to the knee joint to simultaneously align the first rotational axis parallel to the medial/lateral axis of the knee, the second rotational axis parallel to the anterior/posterior axis of the knee, and the translation axis parallel to the proximal/distal axis of the knee such that operating the first rotational adjustment mechanism moves the cut plane in extension plane rotation, operating the second rotational adjustment mechanism moves the cut plane in varus/valgus rotation, and operating the translation adjustment mechanism translates the cut plane parallel to the proximal/distal axis.

* * * * *